United States Patent
Plakas et al.

(10) Patent No.: US 9,773,325 B2
(45) Date of Patent: Sep. 26, 2017

(54) MEDICAL IMAGING DATA PROCESSING APPARATUS AND METHOD

(71) Applicant: Toshiba Medical Systems Corporation, Otawara-shi (JP)

(72) Inventors: Costas Plakas, Edinburgh (GB); Marco Razeto, Edinburgh (GB)

(73) Assignee: Toshiba Medical Systems Corporation, Otawara-shi (JP)

( * ) Notice: Subject to any disclaimer, the term of this patent is extended or adjusted under 35 U.S.C. 154(b) by 0 days.

(21) Appl. No.: 14/677,007

(22) Filed: Apr. 2, 2015

(65) Prior Publication Data

US 2016/0292848 A1    Oct. 6, 2016

(51) Int. Cl.
| G06K 9/00 | (2006.01) |
| G06T 11/00 | (2006.01) |
| A61B 8/08 | (2006.01) |
| G06T 7/11 | (2017.01) |

(52) U.S. Cl.
CPC ............ *G06T 11/003* (2013.01); *A61B 8/085* (2013.01); *A61B 8/5207* (2013.01); *A61B 8/5223* (2013.01); *G06T 7/11* (2017.01); *G06T 2207/10132* (2013.01); *G06T 2207/20156* (2013.01); *G06T 2207/30004* (2013.01); *G06T 2207/30024* (2013.01); *G06T 2207/30242* (2013.01)

(58) Field of Classification Search
None
See application file for complete search history.

(56) References Cited

U.S. PATENT DOCUMENTS

| 6,385,332 | B1* | 5/2002 | Zahalka | 345/156 |
| 8,144,964 | B1* | 3/2012 | Napoli | G06T 7/0081 |
| | | | | 382/131 |
| 8,538,117 | B2* | 9/2013 | Najarian | A61B 6/032 |
| | | | | 378/4 |
| 2002/0048401 | A1* | 4/2002 | Boykov | G06K 9/342 |
| | | | | 382/173 |
| 2004/0008886 | A1* | 1/2004 | Boykov | G06K 9/342 |
| | | | | 382/173 |
| 2004/0258305 | A1* | 12/2004 | Burnham | G06K 9/342 |
| | | | | 382/171 |
| 2005/0249399 | A1* | 11/2005 | Tek | G06T 7/0081 |
| | | | | 382/154 |

(Continued)

FOREIGN PATENT DOCUMENTS

JP      2012-223315 A     11/2012

OTHER PUBLICATIONS

Potocnik et al. ("Automated Ovarian Foolicle Segmentation Using Region Growing", 2009).*

(Continued)

*Primary Examiner* — Avinash Yentrapati
(74) *Attorney, Agent, or Firm* — Oblon, McClelland, Maier & Neustadt, L.L.P.

(57) ABSTRACT

A medical imaging data processing apparatus comprises a setting circuitry configured to set a plurality of seeds at different locations in medical image data, a processing circuitry configured to select at least one seed from among the plurality of seeds and expand the at least one selected seed, and a region identifying circuitry configured to identify at least one target region based on a result of the expansion.

22 Claims, 7 Drawing Sheets

(56) References Cited

U.S. PATENT DOCUMENTS

| | | | | |
|---|---|---|---|---|
| 2008/0019580 | A1* | 1/2008 | Ohyu | G06K 9/3216 382/130 |
| 2008/0019587 | A1* | 1/2008 | Wilensky | G06T 7/0083 382/159 |
| 2009/0097727 | A1* | 4/2009 | Jolly | A61B 6/466 382/131 |
| 2010/0014739 | A1* | 1/2010 | Kiraly | G06K 9/342 382/131 |
| 2010/0183225 | A1* | 7/2010 | Vantaram | G06T 7/0081 382/173 |
| 2010/0296709 | A1* | 11/2010 | Ostrovsky-Berman | G06T 7/0081 382/128 |
| 2012/0250933 | A1* | 10/2012 | Porikli | G06T 7/0081 382/100 |
| 2013/0016884 | A1* | 1/2013 | El-Hilo | G06K 9/00 382/128 |
| 2013/0108133 | A1* | 5/2013 | Inoue | G06T 3/0037 382/131 |
| 2014/0334668 | A1* | 11/2014 | Saund | G06T 7/20 382/103 |
| 2015/0125052 | A1* | 5/2015 | Wong | G06K 9/46 382/128 |
| 2015/0201829 | A1* | 7/2015 | Yang | G01N 21/4795 382/131 |

OTHER PUBLICATIONS

"Ultrasound Imaging: Assisted Reproductive Medicine" GE Healthcare, 2012, 2 Pages.

Terrence Chen, et al., "Automatic ovarian follicle quantification from 3D ultrasound data using global/local context with database guided segmentation" Computer Vision, IEEE 12$^{th}$ International Conference, 2009, 8 Pages.

P.S. Hiremath, et al., "Follicle Detection and Ovarian Classification in Digital Ultrasound Images of Ovaries" Advancements and Breakthroughs in Ultrasound Imaging—Chapter 7, 2013, pp. 167-200.

P.S. Hiremath, et al., "Speckle Noise Reduction in Medical Ultrasound Images" Advancements and Breakthroughs in Ultrasound Imaging—Chapter 8, 2013, pp. 201-242.

* cited by examiner

MEDICAL IMAGING DATA PROCESSING APPARATUS AND METHOD

FIELD

Embodiments described herein relate generally to a method of, and apparatus for, processing medical imaging data, for example for segmenting medical imaging data. Certain embodiments relate, for example, to segmentation of ovarian follicles in ultrasound data.

BACKGROUND

Counting and measurement of ovarian follicles in ultrasound images is a procedure that is performed for fertility assessment in IVF (in vitro fertilization) treatments. The patient's ovaries are regularly scanned with transvaginal ultrasound. The number of ovarian follicles in the ovaries is counted, and the diameter of each ovarian follicle is measured. In some current systems, the diameter of each ovarian follicle is measured manually. The number and diameter of the follicles is tracked over time to assess treatment progress. A steady increase in the number and/or diameter of the follicles may indicate that the patient is responding well to treatment. Once the number and size of the follicles reach a predetermined threshold, eggs will be aspirated, fertilized and re-implanted (or may be frozen).

FIG. 1 is a schematic drawing that is representative of an ultrasound image in which a plurality of follicles 10 are visible. In an ultrasound image, follicles 10 may look like dark chambers.

Segmentation may represent the process of identifying pixels or voxels representing a given structure in an image or set of image data, which may include separating the pixels or voxels from the rest of the image or set of image data. The identification and/or separation of pixels or voxels representing the structure facilitates further processing of information relating to the structure, for example, measurement of the structure, or rendering the structure in a way that is distinct from other structures in the image or set of image data. In order to separate a structure from the rest of the image or set of image data, it is necessary to know which pixels or voxels correspond to which tissue types (or types of artificial object). The image can then be divided into a part of the image or set of image data that represents the tissue type corresponding to the structure, and a remainder that does not represent the tissue type. If there is more than one structure in the image or set of image data of a given tissue type, further techniques may be used to separate discrete structures. Multiple structures may be segmented in one image or set of image data.

BRIEF DESCRIPTION OF THE DRAWINGS

Embodiments are now described, by way of non-limiting example, and are illustrated in the following figures, in which.

DETAILED DESCRIPTION

Certain embodiments provide a medical imaging data processing apparatus comprising a setting circuitry configured to set a plurality of seeds at different locations in medical image data, a processing circuitry configured to select at least one seed from among the plurality of seeds and expand the at least one selected seed, and a region identifying circuitry configured identify at least one target region based on the expansion.

Certain embodiments provide a medical imaging data processing method comprising setting a plurality of seeds at different locations in medical image data, selecting at least one seed from among the plurality of seeds and expanding the at least one selected seed, and identifying at least one target region based on a result of the expansion.

Figure 1:
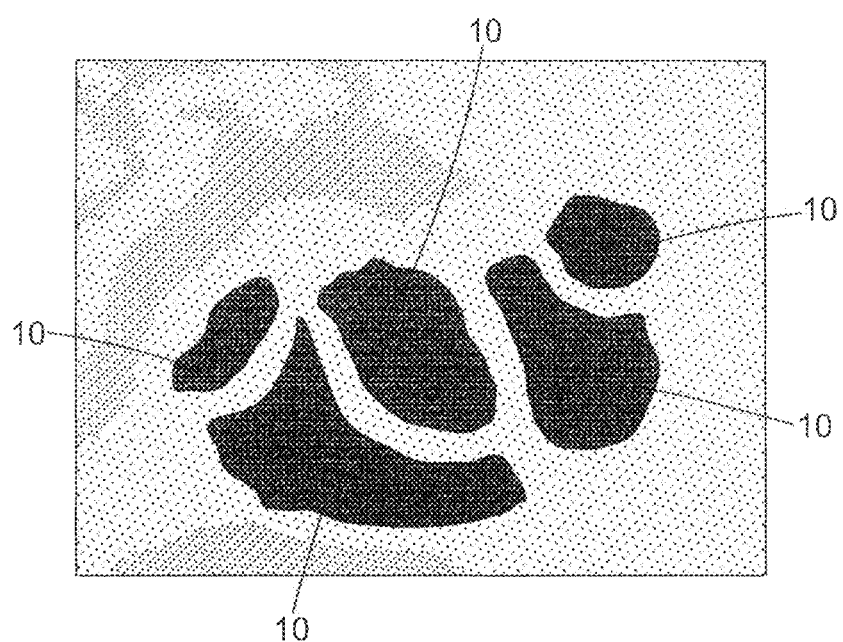
FIG. 1 is representative of an ultrasound image showing a plurality of follicles.
Figure 2:
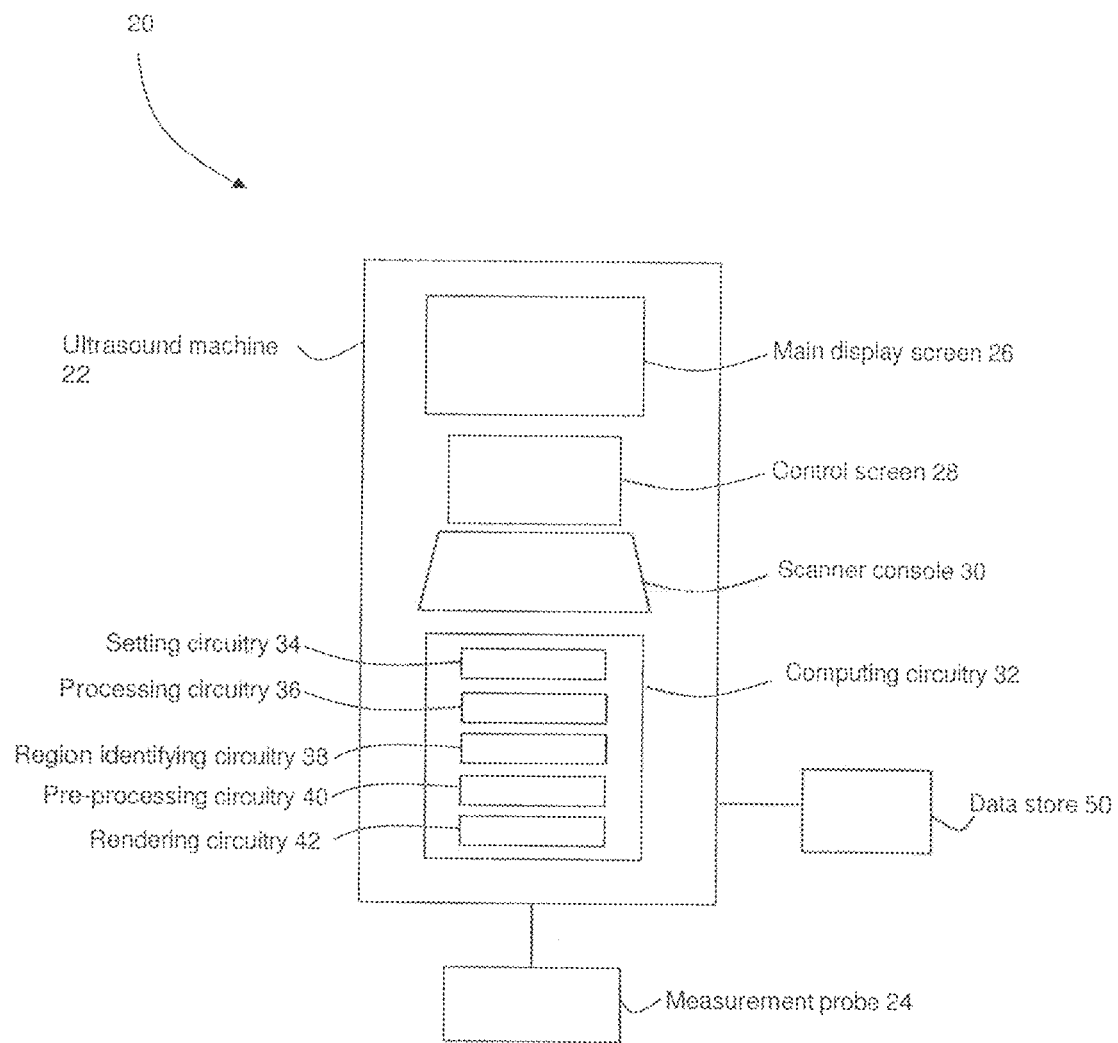
FIG. 2 is a schematic diagram of a diagnostic apparatus according to an embodiment.

An apparatus 20 according to an embodiment is illustrated schematically in FIG. 2. Apparatus 20 is configured to acquire data from a medical imaging scan and to process the acquired data to segment one or more desired anatomical structures. In the present embodiment, the apparatus 20 processes images and/or image data and may be used as part of a diagnostic process. The apparatus 20 in this embodiment may be considered to be a medical diagnostic apparatus and a medical imaging data processing apparatus.

In the present embodiment, apparatus 20 comprises an ultrasound machine 22 and associated probe 24. Any suitable type of ultrasound machine 22 and probe 24 may be used, for example any ultrasound machine 22 and probe 24 that are configured to obtain ultrasound image data that is suitable for 2D, 3D or 4D imaging. In other embodiments the apparatus 20 may comprise a scanner of an alternative modality, for example a CT scanner, cone-beam CT scanner, X-ray scanner, MR scanner, PET scanner or SPECT scanner.

The ultrasound machine 22 comprises a main display screen 26 for displaying a main ultrasound image, a control screen 28 for displaying control information, and a scanner console 30. In this embodiment, the scanner console 30 comprises an input device or devices such as input buttons or knobs, a computer keyboard, a mouse or a trackball. In alternative embodiments, the control screen 28 is a touch screen, which is both a display device and a user input device. Further embodiments may comprise a control screen 28, display screen or main display screen 26 that does not form part of the ultrasound machine 2. The ultrasound machine 22 also comprises a data store 50 for storing image data.

The ultrasound machine 22 comprises computing circuitry 32 for processing of data, including image data. The computing circuitry 32 comprises setting circuitry 34 for placing seeds, processing circuitry 36 for selecting seeds and expanding selected seeds, and region identifying circuitry 38 for identifying target regions. In the present embodiment, the computing circuitry 32 also comprises pre-processing circuitry 40 and rendering circuitry 42. In some embodiments, the computing circuitry 32 may also comprise diagnosis circuitry for performing a diagnosis.

The computing circuitry 32 also includes a hard drive and other components including RAM, ROM, a data bus, an operating system including various device drivers, and hardware devices including a graphics card. Such components are not shown in FIG. 2 for clarity.

Figure 3:
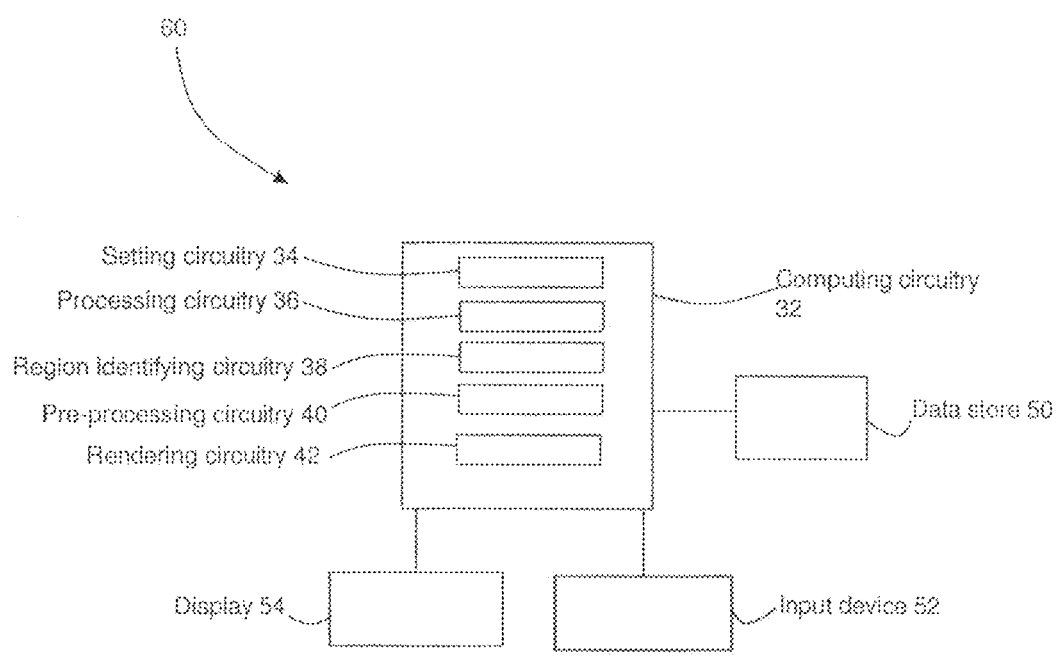
FIG. 3 is a schematic diagram of an imaging data processing apparatus according to an embodiment.

An alternative embodiment is illustrated in the schematic diagram of FIG. 3. An apparatus 60 is configured to receive data that has previously been acquired by a separate scanner (such as an ultrasound machine, CT scanner, cone-beam CT scanner, X-ray scanner, MR scanner, PET scanner or SPECT scanner), and to process the received data to segment one or more anatomical structures. Apparatus 60 comprises computing circuitry 32 comprising setting circuitry 34, processing circuitry 36 and region identifying circuitry 38. In the embodiment of FIG. 3, computing circuitry 32 also comprises pre-processing circuitry 40 and rendering circuitry 42. Apparatus 60 may comprise any suitable PC, workstation, terminal, tablet or other suitable computing apparatus. Apparatus 60 comprises at least one input device 52, for example a keyboard, mouse or touchscreen, and at least one display 54. Image processing apparatus 60 further comprises a data store 50. Apparatus 60 may be described as an image processing apparatus.

In the embodiments of FIG. 2 and FIG. 3, setting circuitry 34, processing circuitry 36 and region identifying circuitry 38 are each implemented in computing circuitry 32 by means of a computer program having computer-readable instructions that are executable to perform the method of the embodiment. However, in other embodiments each of the setting circuitry 34, processing circuitry 36 and region identifying circuitry 38 may be implemented in software, hardware or any suitable combination of hardware and software. In some embodiments, the various circuitries may be implemented as one or more ASICs (application specific integrated circuits) or FPGAs (field programmable gate arrays).

Figure 4:
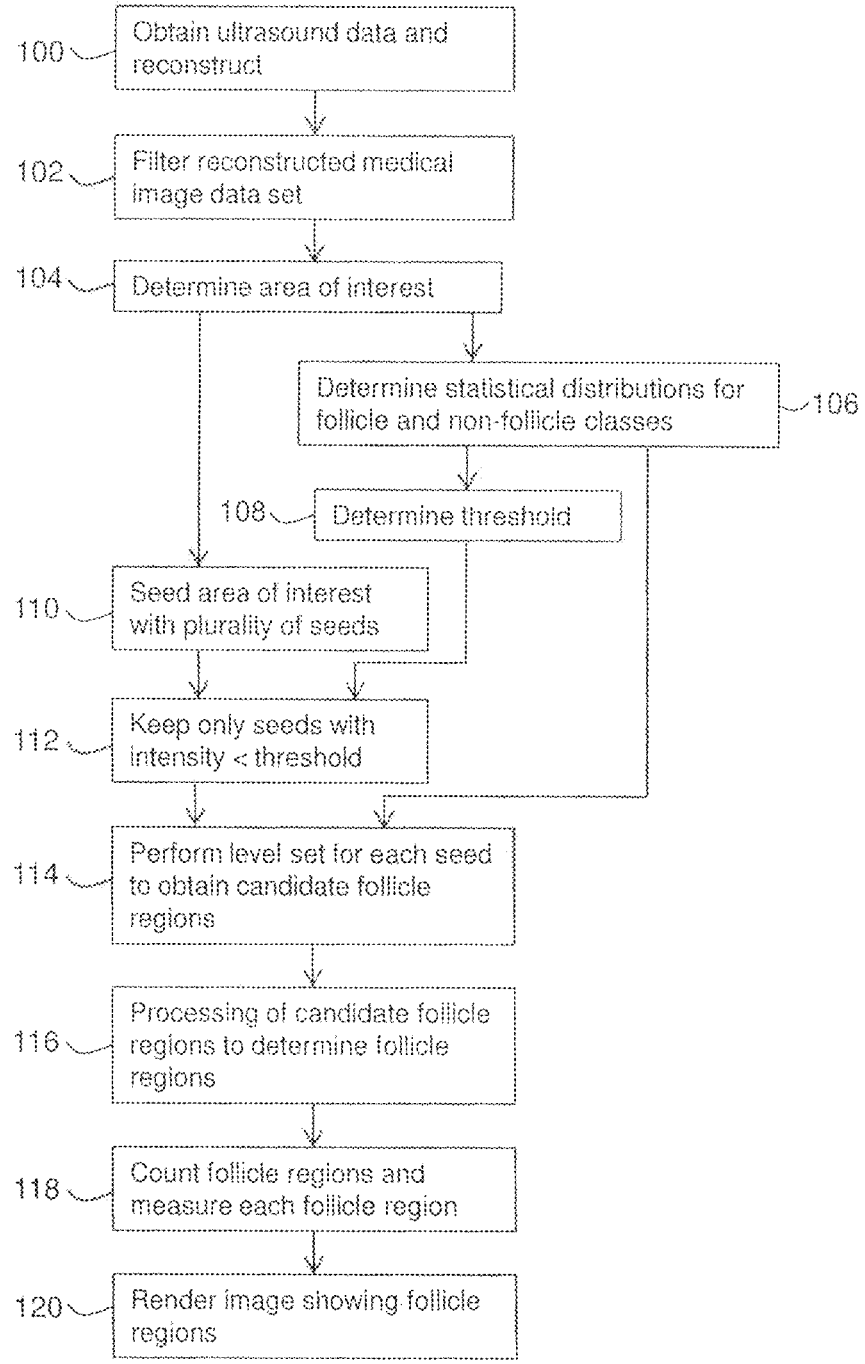
FIG. 4 is a flowchart illustrating in overview the process of a first embodiment.

The system of FIG. 2 is configured to perform a process having a series of stages as illustrated in overview in the flow chart of FIG. 4.

At stage 100, raw ultrasound data is acquired by the ultrasound machine 22 using the probe 24. The raw ultrasound data is representative of echo signals obtained by ultrasonic transmission and reception to and from a three-dimensional anatomical region of the subject. In the present embodiment, the anatomical region comprises the abdomen of a patient. In other embodiments, the region may comprise the heart and chest region, the limbs, the neck, the head, or any other part of the human or animal body. Stage 100 may be referred to as an image acquisition phase.

The pre-processing circuitry 40 performs a reconstruction of the raw ultrasound data to obtain a medical image data set. The medical image data set comprises an array of voxels. Each voxel has a position and an associated signal intensity. Different tissue types may produce different signal intensities. In alternative embodiments, the medical image data set may be a two-dimensional data set comprising an array of pixels. The rendering circuitry 42 renders an image from the medical image data set and displays the rendered image on main display screen 26. In other embodiments, no image may be rendered at stage 100, or an image may be rendered but not displayed.

At stage 102, the pre-processing circuitry 40 applies a filter to the medical image data set. In the present embodiment, the filter comprises a median filter, which preserves edges while removing noise. In other embodiments, the pre-processing circuitry 40 applies an anisotropic diffusion filter instead of or in addition to the median filter. In further embodiments, any appropriate filter may be used, for example a speckle removing filter. Examples of speckle reducing filters may include Lee filters, Kuan filters, Wiener filters or wavelet transform filters (see, for example, chapter 8 of 'Advancements and Breakthroughs in Ultrasound Imaging', edited by Gunti Gunarathne, ISBN 978-953-51-1159-7). The filter may comprise a noise-reducing filter. The filter may be intended to improve the image quality of an image rendered from the medical image data set. In alternative embodiments, no filtering is performed and stage 102 is omitted.

At stage 104, the pre-processing circuitry 40 identifies a three-dimensional area of interest in the medical image data set. In the present embodiment, the medical image data set is representative of the abdomen of the patient and the rendered image is an image of the abdomen of the patient. A user (for example, a radiologist, clinician or technician) selects a part of the rendered image that represents the patient's ovary, for example by drawing a box around a part of the rendered image. The pre-processing circuitry 40 identifies a three-dimensional area of interest in the medical image data set that corresponds to the selected part of the rendered image. In other embodiments, the area of interest may be two-dimensional. By identifying a user-supplied area of interest around the ovary, subsequent computations may be made simpler.

In some embodiments, the pre-processing circuitry 40 automatically identifies a two-dimensional or three-dimensional area of interest. In one embodiment, the pre-processing circuitry 40 performs an initial segmentation of the patient's ovary in the medical image data set and identifies an area of interest in the medical image data set that corresponds to the initial segmentation of the ovary. In further embodiments, a part of the medical image data set that is representative of the center of the imaged region is identified as the area of interest. In alternative embodiments, the entire medical image data set is identified as the area of interest.

In further embodiments, no area of interest is selected and subsequent steps are performed on the entire medical image data set.

Stages 102 and 104 may be referred to as pre-processing stages. The medical image data set may be pre-processed to identify an area of interest and/or to optimize appearance. In further embodiments, additional pre-processing stages may be performed by the pre-processing circuitry 40. The pre-processing stages may comprise steps that would make the step of statistical estimation at stage 106 easier, for example by reducing noise in the data or by removing irrelevant parts of the medical image data set. The pre-processing stages may be performed in any order. For example, in some embodiments, the identification of the area of interest may be performed before applying a filter to the medical image data set. In some embodiments, an image is rendered from the medical image data set after some or all of the pre-processing steps have been performed.

The processing circuitry 36 is configured to distinguish between follicle tissue and non-follicle tissue by estimating statistical distributions of intensity for each of two classes (a follicle tissue class and a non-follicle tissue class) using a statistical estimation method. The statistical estimation method may comprise, for example, Multivariate Gaussian classification, Support Vector Machines, Decision Forests, or an Expectation Maximization algorithm. Follicle tissue may be tissue that is inside an ovarian follicle. Non-follicle tissue may be tissue that is not inside an ovarian follicle.

The statistical estimation method has previously been trained on a plurality of sets of training data. The sets of training data may be medical image data sets that have been manually segmented to distinguish follicle tissue from non-follicle tissue. The statistical estimation method may learn from the training data in an offline (non-real time) process. The details of the training method may depend on the specific algorithm and on the number of classes for which the machine is training. In some embodiments, more than two classes may be trained. For example, in one embodiment, the classes that are trained comprise a class for follicle, a class for edge of follicle, and a class for soft tissue.

In other embodiments, the processing circuitry 36 may be configured to distinguish between a target class which comprises tissue belonging to a desired anatomical structure, and at least one further class which comprises tissue that does not belong to the desired anatomical structure.

Each class may comprise tissue of a particular tissue type. In some embodiments, classes may comprise tissue of more than one tissue type. For example, a class may comprise all tissue that is part of an anatomical structure of interest, and the anatomical structure of interest may comprise more than one tissue type. A further class may comprise all tissue that is not part of the anatomical structure of interest. The further class may comprise several different tissue types. In some circumstances, different tissue types in a given class (for example, different tissue types that are part of a single anatomical structure) may have similar imaging properties.

At stage 106, the processing circuitry 36 obtains a histogram representing the intensity values of voxels in the area of interest. In general the processing circuitry would not usually display the histogram, although it could if so desired, but would generate histogram data. The processing circuitry 36 then fits a first statistical distribution of intensity value and a second statistical distribution of intensity value to the histogram using a statistical estimation method. Voxels having intensity values in the first distribution may be representative of follicle tissue. Voxels having intensity values in the second distribution may be representative of non-follicle tissue.

In the present embodiment, the processing circuitry 32 assumes that each statistical distribution is a Gaussian distribution. The processing circuitry 32 estimates a mean and standard deviation for each Gaussian distribution. In other embodiments, any suitable distribution may be used. The two statistical distributions have different peak values, but may overlap. Voxels may be assigned a likelihood or probability of belonging to follicle tissue or to non-follicle tissue based on the statistical distributions.

In the present embodiment, the statistical distributions are estimated using the intensities of voxels in the area of interest, after any pre-processing has been carried out. In other embodiments, the statistical distributions may be estimated using the intensities of all the voxels in the medical image data set, or the intensities of voxels in a subset of the medical image data set. In alternative embodiments, the medical image data set comprises an array of pixels, and statistical distributions are estimated using the intensities of at least part of the array of pixels.

In the present embodiment, the statistical distributions are statistical distributions of individual voxel intensity. In other embodiment, parameters other than individual voxel intensity may be used. For example, an average voxel intensity value in the neighborhood of a voxel may be used, or a gradient value may be used. Other parameters that may be used individually or in combination may include for example the shape of the region grown, local gradient, texture appearance indicators (for example, Gabor filters), or higher order derivatives (for example, Hessian matrix or local divergence).

In the present embodiment, two statistical distributions are estimated. The statistical distributions correspond to two classes of tissue: follicle tissue and non-follicle tissue. In other embodiments, three or more statistical distributions may be estimated. In one embodiment, a first statistical distribution is estimated for follicle tissue. A second statistical distribution is estimated for tissue that is outside follicles (which does not include tissue that lies between follicles). A third statistical distribution is estimated for tissue that lies between follicles.

In further embodiments, several statistical distributions may be estimated for different types of non-follicle tissue. Tissue outside follicles may be very diverse, so it may be useful to split the voxels outside the follicles into multiple classes, each having its own statistical distribution. The number of classes (for example, two, three or four classes) may be pre-determined by the system.

At stage 108, the processing circuitry 36 determines a threshold intensity value in dependence on the estimated statistical distributions for the follicle tissue and non-follicle tissue. The threshold value is chosen such that there is a high probability (for example, 95% or 99%) of intensities below the threshold corresponding to follicle tissue. In the present embodiment, two estimated statistical distributions are used to determine the threshold, and the same two estimated statistical distributions are used to grow candidate regions at stage 116. In some embodiments, two estimated distributions (for follicle tissue and non-follicle tissue) are used to determine the threshold, but a larger number of estimated distributions (for example, distributions for follicle tissue, tissue outside follicles and tissue between follicles) are used to grow candidate regions at stage 116.

In alternative embodiments, no threshold value is determined at stage 108. In some embodiments, a fixed threshold value is pre-determined (for example, from training data) and is stored in the processing circuitry 36 before the process of FIG. 4 begins. In some embodiments, the user may select a threshold value.

Figure 5:
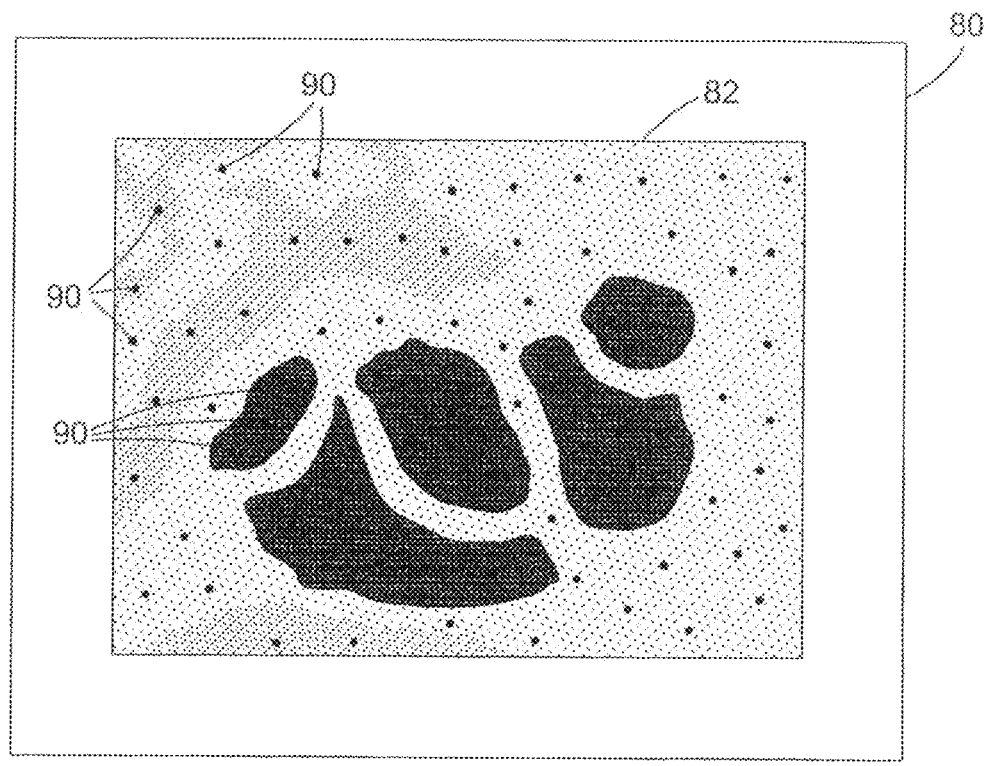
FIG. 5 is a schematic diagram showing an area of interest on which seeds are distributed.

At stage 110, the setting circuitry 34 sets a plurality of seeds 90 at different locations in the area of interest. FIG. 5 is a schematic diagram that is representative of an image 80 comprising an area of interest 82. Seeds 90 are placed across the area of interest 82.

In the present embodiment, the seeds 90 are individual voxels. In other embodiments, the seeds 90 may comprise points, pixels, voxels, two-dimensional regions or three-dimensional regions. In the present embodiment, the setting circuitry 34 distributes seeds 90 pseudorandomly across the area of interest 82. The seeds 90 may be placed at unequal distances. The pseudorandom positions of the seeds 90 are generated by a Halton sequence. In other embodiments, any suitable algorithm may be used to determine a pseudorandom placing of the seeds 90. In further embodiments, any suitable method of placing seeds 90 and any suitable arrangement of seeds 90 in the area of interest 82 may be used. In some embodiments, the plurality of seeds 90 is distributed in a regular configuration rather than pseudorandomly. Seeds 90 may be placed at equal spacings across the area of interest 82, for example in a grid configuration comprising seeds 90 distributed at equal distance.

The seeds 90 are distributed at a density such that at least one seed is likely to be placed in each follicle of the ovary. The present embodiment has a density of seeds 90 such that it is likely that a plurality of seeds will be placed in each follicle. Using a plurality of seeds may make the process of FIG. 4 faster. In embodiments having regular seed spacings, the seed spacing may be chosen such that it is likely that each follicle will contain at least one seed 90.

At stage 112, the processing circuitry 36 determines whether each seed 90 belongs to follicle tissue. In the present embodiment, each seed 90 is an individual voxel. For each seed 90, the processing circuitry 36 compares the intensity value of the voxel to the threshold value determined at stage 108 to determine whether the seed 90 belongs to follicle tissue. If the intensity value is below the threshold value, the processing circuitry 36 determines that the seed 90 belongs to follicle tissue. The processing circuitry 36 selects the seeds 90 that are determined to belong to follicle tissue. The processing circuitry 36 discards the seeds 90 that are not determined to belong to follicle tissue. The processing circuitry 36 may keep only seeds 90 for which there is a high level of confidence that the seeds are inside follicles (based on the statistics calculated at stage 106). In practice, if a strict threshold value is used, some of the discarded seeds may in fact belong to follicle tissue but may not meet the threshold. However, the density of seeds 90 may be such that even if some seeds 90 that belong to follicle tissues are discarded, there will still be at least one selected seed 90 in each follicle.

Figure 6:
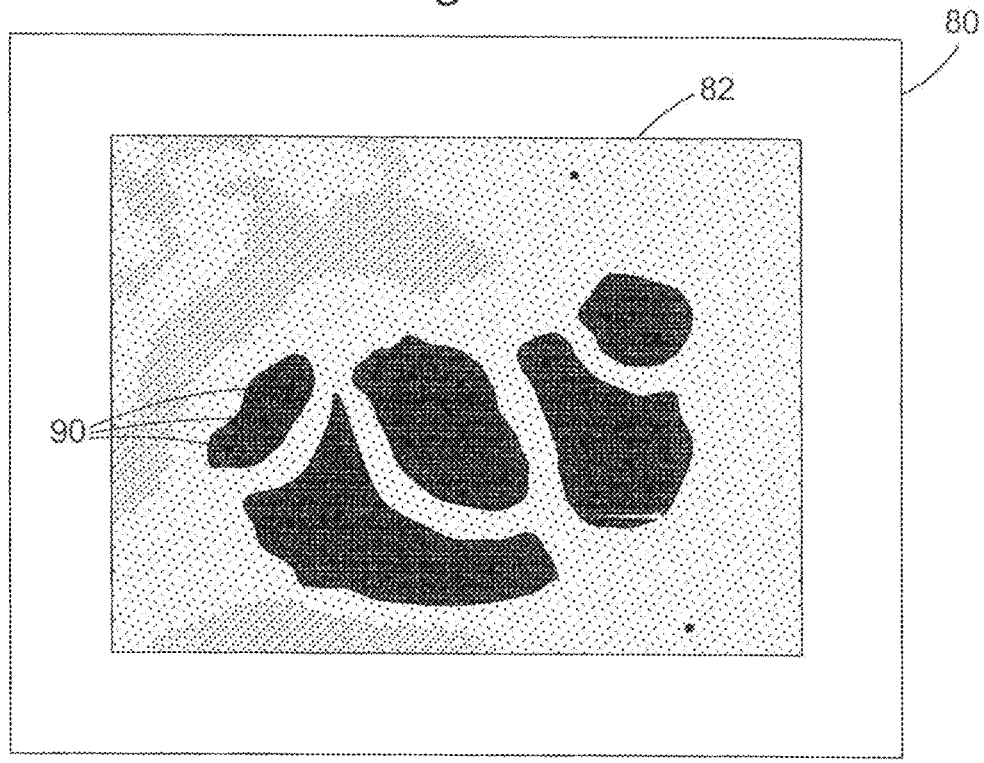
FIG. 6 is a schematic diagram illustrating an area of interest with selected seeds.

FIG. 6 is a schematic diagram that is representative of the image 80 comprising an area of interest 82 that is also represented in FIG. 5. In FIG. 6, fewer seeds 90 are shown than in FIG. 5. The seeds 90 that are shown in FIG. 6 are seeds that have passed an intensity threshold and have been determined to belong to follicle tissue.

In some embodiments, each seed 90 is a point which may or may not be coincident with a voxel. An intensity value for the point is interpolated from neighboring voxels and compared with the threshold value. In other embodiments, each seed 90 is a two- or three-dimensional region. Any suitable intensity value for the seed region may be compared with the threshold value. For example, an average, maximum or minimum intensity value for the seed region may be compared with the threshold value to determine whether the seed region belongs to follicle tissue.

In further embodiments, a different method of determining whether at least part of a seed belongs to follicle tissue is used. In some embodiments, a threshold value is used for a different parameter rather than for individual voxel intensity. In some embodiments, for each voxel, the processing circuitry 36 determines a likelihood that the voxel belongs to follicle tissue, and selects voxels having a high likelihood of belonging to follicle tissue. The likelihood may be determined using parameters of the voxel itself and/or parameters relating to the local neighborhood of the voxel.

In ultrasound, follicles present as dark regions and therefore seeds below an intensity threshold are determined to belong to follicle tissue. For different structures and/or different modalities, desired anatomical structures may present as bright regions, and seeds above an intensity threshold may be determined to belong to a target class for the desired anatomical structure.

At stage 114, the processing circuitry 36 grows the seeds 90 that were selected at stage 112 into candidate follicle regions. The processing circuitry 36 determines whether voxels adjacent to a selected seed 90 belong to follicle tissue. If so, the processing circuitry 36 may expand a region starting from the selected seed to include the adjacent voxels. The region may be called a candidate follicle region. The processing circuitry 36 may continue to expand the candidate follicle region until reaching a boundary where adjacent voxels do not belong to follicle tissue. In the present embodiment, all the seeds 90 are grown into candidate follicle regions simultaneously. As candidate follicle regions are expanded, they may touch or overlap. In some embodiments, candidate follicle regions that touch or overlap during the growing process are merged with each other and the merged candidate follicle region may be grown further. In some embodiments, candidate follicle regions are allowed to overlap at the growing stage of stage 114, and overlaps are resolved later, for example at stage 116. Although in the present embodiment the candidate follicle regions are grown simultaneously, in other embodiments the candidate follicle regions may be grown one at a time.

In the present embodiment, the processing circuitry 36 grows the seeds 90 using a level set algorithm. The level set algorithm decides how to grow each seed 90 into a candidate follicle region 92 based on whether adjacent voxels belong to follicle tissue or non-follicle tissue. The level-set algorithm uses the statistical distributions determined at stage 106 to distinguish between follicle tissue and non-follicle tissue. In some embodiments, multiple types of non-follicle tissue may be distinguished. The processing circuitry 36 may determine a likelihood that each voxel belongs to each tissue class, and use the determined likelihoods in the level set. In some circumstances, the level set algorithm may be capable of growing a given seed into more than one candidate follicle region 92.

The level-set algorithm also implements shape and smoothness constraints on the growing of the candidate follicle regions 92. The tissue class statistics from stage 106 govern the level set grown along with the shape and smoothness constraints.

In the event that a seed 90 was incorrectly identified as belonging to follicle tissue, the seed may not grow under the level set and may be removed in processing.

In other embodiments, any suitable region growing algorithm may be used instead of a level set algorithm. In the present embodiment, seeds are grown into candidate follicle regions 92 in dependence on intensity values of individual voxels. In some embodiments, the level set algorithm may grow seeds into candidate follicle regions 92 in dependence on the local environment of each voxel, for example in dependence on an average intensity in a small area around each voxel, or in dependence on gradient values.

Each of the candidate follicle regions 92 may comprise a connected region of voxels that are likely to be follicle tissue. However, as described above, multiple seeds may be placed in one follicle, and therefore that follicle may comprise multiple candidate follicle regions 92. In some circumstances, some voxels may be mis-identified as follicle tissue or as non-follicle tissue. In some cases, a single candidate follicle region 92 may be grown into more than one follicle.

Figure 7:
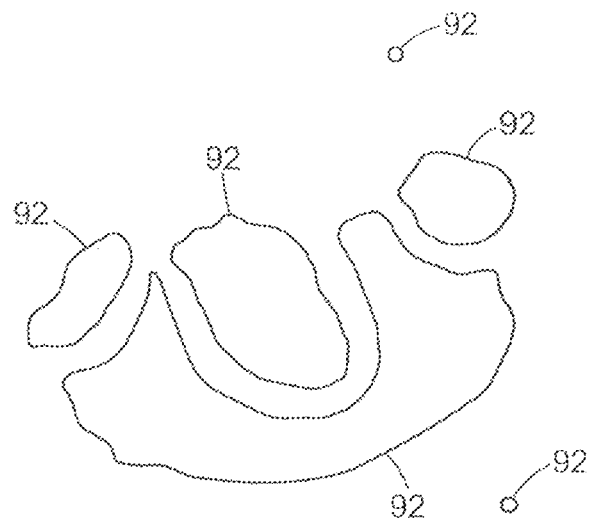
FIG. 7 is a schematic diagram showing a set of candidate follicle regions.

FIG. 7 is a schematic diagram representing a set of candidate follicle regions 92 that have been identified in the area of interest 82 shown in FIGS. 5 and 6.

At stage 116, the region identifying circuitry 38 processes the candidate follicle regions 92 to identify follicles 94 in the medical image data set. Identifying a follicle 94 may comprise defining a region of voxels, which may be described as a target region. Identifying a follicle 94 may comprise identifying which voxels are part of the target region and which voxels are not part of the target region. Identifying a follicle 94 may comprise segmenting a follicle 94. A plurality of follicles 94 may each be identified. Processing of the candidate follicle regions 92 to identify follicles 94 may be referred to as post-processing.

In the present embodiment, the region identifying circuitry 38 performs size discrimination to rule out candidate follicle regions 92 that do not have an appropriate size, for example candidate follicle regions 92 that are very small. The region identifying circuitry 38 then performs fusion of overlapping objects. The region identifying circuitry 38 performs a shape discrimination to rule out candidate follicle regions 92 that have an inappropriate shape, for example candidate follicle regions 92 that are very elongated. The region identifying circuitry 38 then performs a morphological separation based on shape analysis. The region identifying circuitry 38 may perform a second pass of shape discrimination on the separated object. The region identifying circuitry 38 performs a smoothing of the resulting follicle regions 94.

In other embodiments, processing the candidate follicle regions 92 may comprise performing shape and size discrimination on the candidate follicle regions 92 to select candidate follicle regions 92 that have an appropriate shape and size to be a follicle 94. For example, very small candidate follicle regions 92 may be eliminated. Selecting candidate follicle regions 92 that have an appropriate shape and size may prevent dark areas resulting from echoic shadows from being incorrectly identified as follicles 94.

Figure 8:
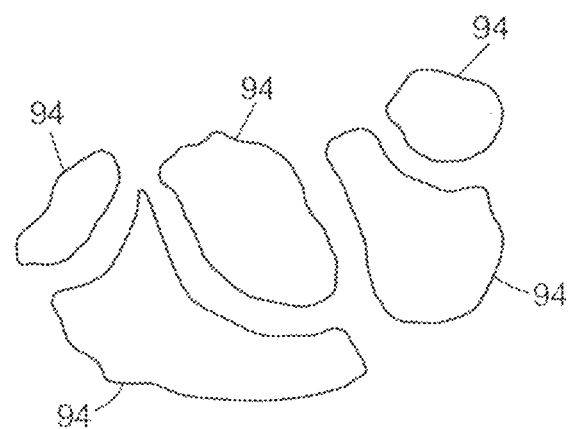
FIG. 8 is a schematic diagram showing a set of follicles.

Processing the candidate follicle regions 92 may further comprise applying morphological operations to the candidate follicle regions 92. The region identifying circuitry 38 may apply morphological operations to merge candidate follicle regions 92 that are wrongly separated, in which a single follicle 94 presents as two or more candidate follicle regions 92. Adjacent or overlapping candidate follicle regions 92 may be combined to form a single target region. The region identifying circuitry 38 may apply morphological operations to separate candidate follicle regions 92 that are wrongly fused, for example where two follicles 94 are contained in a single candidate follicle region 92. FIG. 8 shows a set of follicles 94 that may result from post-processing of the candidate follicle regions 92 of FIG. 7. The two smallest candidate follicle regions 92 have been removed because of their size. The largest candidate follicle region 92 has been identified as representing two follicles 94 and has therefore been split into two.

A smoothing filter may also be applied to the candidate follicle regions 92. The smoothing filter may smooth the appearance of the follicles 94 when an image is rendered from the medical image data set.

Any of the morphological operations, shape and size discrimination and smoothing filter may be altered or omitted, and further processing operations may be added. The processing operations may be performed in any order.

Applying the processing operations to the candidate follicle regions 92 results in at least one target region of voxels. The or each target region may be considered to be a segmentation of an individual follicle. In other embodiments, any desired anatomical structure may be identified. Distributions for at least two classes are estimated at stage 106. At least one of the classes corresponds to a tissue type of the desired anatomical structure. Candidate regions are determined at stage 114 and are processing at stage 116 to obtain at least one target region. Each target region is identified as a desired anatomical structure. Desired anatomical structures may comprise, for example cysts or other air or water pockets in other tissue, heart chambers, certain types of tumors or growths, or other self-contained structures displaying a different overall brightness from the surrounding tissue. In other embodiments, desired anatomical structures may comprise hyperechoic tumors, for example, liver, spleen, renal, and other abdominal metastases.

The desired anatomical structure may comprise a pathological structure, such as a gall stone, kidney stone, cyst, or area of the lung affected by emphysema.

In further embodiments, a class may comprise material belonging to an artificial structure. For example, a class may correspond to a type of man-made implanted object such as implanted radiation therapy seeds. Target regions may be determined which correspond to a particular type of artificial structure.

Target regions may be regions that have a different response to ultrasound than surrounding tissue. Target regions may be regions of hypoechoic (dark) tissue, as is the case with follicles. In other embodiments, target regions may be regions of hyperechoic (bright) tissue. In further embodiments, target regions may be regions that respond differently to the modality used (for example, regions that respond differently to CT, MR, PET, SPECT or X-ray).

At stage 118, the region identifying circuitry 38 counts the number of follicles. The number of target regions may be expected to be representative of the number of follicles in the ovary. The region identifying circuitry 38 measures the size of each of the follicles by measuring each target region. In the present embodiment, the region identifying circuitry 38 measures the volume of each follicle and measures the maximum diameter of each follicle.

In other embodiments, any suitable measurement of each follicle may be performed. For example, a follicle may be measured along a particular axis or in a particular plane. In general, follicles are not spherical, so measurements of a particular diameter may be required, which may require taking measurements at a particular angle. In some embodiments, a geometrical shape such as an ellipsoid (or ellipse) may be fitted to a target region. The volume or area of the geometrical shape may be used to estimate the size of the follicle. In some embodiments, a position of the follicle may be determined.

The measurements obtained, for example the number and size of follicles, may be used to assess potential for harvesting eggs.

In a further embodiment, apparatus 20 comprises diagnostic circuitry that is configured to obtain a diagnosis based on information that has been determined, for example based on the determined size and shape of each follicle or on the number of follicles.

At stage 120, the rendering circuitry 42 renders an image from the medical image data set. Each follicle is rendered such that it may be visually distinguished from the rest of the rendered image. In the present embodiment, each follicle is rendered in a different color, and each of the final follicle region colors is different from the color or colors of parts of the image that are not representative of follicles. In other embodiments, any suitable rendering method may be used in which the follicles are distinguished. In some embodiments, only the follicles may be rendered and displayed without surrounding tissue.

The rendering circuitry 42 displays the rendered image in which the follicles are distinguished on main display screen 26. In the present embodiment, the rendering circuitry 42 also displays a numerical value for the measured size (for example, volume and/or diameter) of each of the follicles on main display screen 26. In other embodiments, the numerical values may be displayed without rendering an image at stage 116. For example, an image rendered at stage 100 (in which the follicles are not visually distinguished) may continue to be displayed along with the determined numerical values. Stage 120 may be referred to as a display phase of at least one identified target region.

The rendered image and/or numerical values for the number and size of follicles may be stored to the patient's medical record.

The method of FIG. 4 may be used to automatically segment, count and measure follicles in a medical image data set. Automatic three-dimensional segmentation of follicles can be used to automate the counting and measurement of follicles, potentially saving time and reducing measurement error. Automatic segmentation and measurement may in some circumstances be more accurate and/or repeatable than manual measurement. Some measurements, for example particular diameters, may be more easily identified using automatic methods. The method of FIG. 4 may be convenient for a user. The user may only have to select an area of interest, for example an ovary. In some embodiments, the user may not have to provide any input to the process of identifying follicles. The user may be able to concentrate on achieving a good ultrasound scan image in real time without having to also perform manual follicle measurements.

Figure 9:
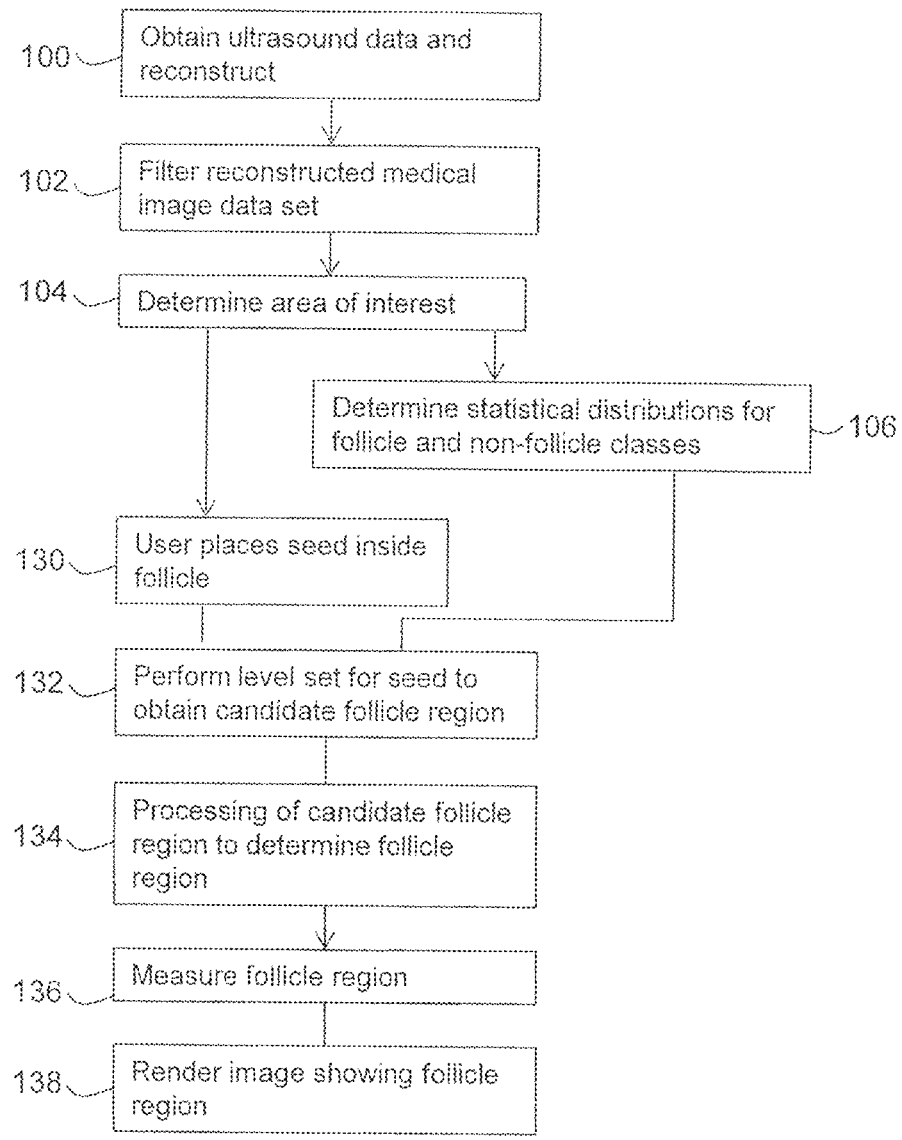
FIG. 9 is a flowchart illustrating in overview the process of a second embodiment.

In a further embodiment, illustrated in the flow-chart of FIG. 9, a user places a seed inside a region of an image that the user has identified as being a follicle. The follicle in which the user has placed the seed is segmented and measured. The method of FIG. 9 is performed using apparatus 20 of FIG. 2.

At stage 100 of FIG. 9, raw ultrasound data is obtained from probe 24. The pre-processing circuitry 40 reconstructs the raw ultrasound data to provide a medical image data set. The rendering circuitry 42 renders an image from the medical image data set and displays the rendered image. At stage 102, the pre-processing circuitry 40 filters the medical image data set using median and/or anisotropic filtering, or any other suitable filtering. At stage 104, the user selects a part of the rendered image that includes an ovary of the patient, and the pre-processing circuitry 40 selects an area of interest in the medical image data set based on the user's selection. In other embodiments, the area of interest may be determined automatically.

At stage 106, the processing circuitry 36 estimates a first statistical distribution of intensity for follicle tissue and a second statistical distribution of intensity for non-follicle tissue. The method of FIG. 9 then proceeds to stage 130.

At stage 130 the user places a seed on the rendered image by clicking a point on the rendered image. In other embodiments, any other method of placing a seed may be used. The user places the seed at a point that the user believes to be inside a follicle. The setting circuitry 34 positions a seed at the point that the user has clicked on. In the present embodiment, the seed is a point. The setting circuitry 34 determines an intensity for the point based on the intensity of the nearest voxel, or based on the intensities of a plurality of neighboring voxels. In other embodiments, the seed may comprise a voxel, pixel, two-dimensional region or three-dimensional region. Any suitable method may be used to obtain user input from which the setting of the seed may be determined.

At stage 132, the processing circuitry 36 grows the seed into a candidate follicle region. The processing circuitry 36 may grow the seed into a candidate follicle region that includes neighboring voxels that are identified as follicle tissue. In the present embodiment, the processing circuitry 36 grows the seed using a level set algorithm which expands the seed in dependence on the voxel intensities and in dependence on shape and smoothness constraints. In other embodiments, any suitable region growing algorithm may be used.

At stage 134, the region identifying circuitry 38 processes the candidate follicle region to obtain a target region. Any suitable processing method may be used. For example, the region identifying circuitry 38 may perform morphological operations, size and shape discrimination and/or filtering. The output of stage 134 is a target region which is identified as a follicle.

At stage 136, the region identifying circuitry 38 measures the volume and/or diameter of the follicle. At stage 138, the rendering circuitry 42 renders an image from the medical image data set in which the follicle is distinguished from the rest of the image. The rendering circuitry 42 may also display a numerical value for the follicle size.

The user may then place a further seed in a different follicle of the newly rendered image (or on the initially rendered image). Stages 130 to 138 may be repeated for the further seed. Although in the present embodiment one seed is placed at a time, in other embodiments the user may place multiple seeds, one for each follicle identified by the user. In such embodiments, two or more seeds may be grown into candidate regions at the same time.

In further embodiments, the seed is a seed region of the rendered image that is identified by the user. In some embodiments, the seed region is a two- or three-dimensional box. In one embodiment, the user draws a box around a single follicle, as identified by the user on the rendered image. The setting circuitry 34 determines a seed region in the medical image data set that corresponds to the box that has been drawn by the user. The processing circuitry 36 applies a level set algorithm to the seed region. Since the seed region is larger than the follicle, the level set algorithm shrinks the seed region into a candidate follicle region by removing parts of the seed region that do not correspond to follicle tissue. The level set algorithm may shrink the seed region until a boundary between follicle tissue and non-follicle tissue is reached. In other embodiments, the level set algorithm may vary the extent of the seed region in any suitable manner, for example by expanding or shrinking the seed region to obtain a candidate follicle region.

Although the process of FIG. 9 requires some user input for each follicle (placing a seed at stage 130) the user is not required to manually measure and/or count follicles. By automating the segmentation, counting and measurement of follicles, follicles may be counted and measured more accurately. The process may be convenient for the user. Only a single click may be required to obtain measurements of each follicle. The user may not have to determine, for example, the boundaries of the follicle or the longest axis of the follicle.

Each of the embodiments of FIG. 4 and FIG. 9 comprises an ultrasound measurement that is performed using an ultrasound machine 22 and probe 24. The embodiments of FIG. 4 and FIG. 9 may be performed in real time, for example during an ultrasound examination. However, in further embodiments, follicle regions may be determined for stored ultrasound image data.

In one embodiment, the image processing apparatus 60 of FIG. 3 is used to process a medical image data set that has been previously obtained from an ultrasound scan. The medical image data set comprises a set of voxels with associated intensities. The pre-processing circuitry 40 of image processing apparatus 60 pre-processes the medical image data set by filtering the medical image data set and obtaining an area of interest. In other embodiments, filtering and/or determining an area of interest may have been performed on the medical image data set before it was stored.

The setting circuitry 34 of image processing apparatus 60 sets a plurality of seeds in the medical image data set. The processing circuitry 36 determines which seeds are inside a follicle by thresholding, and selects seeds that are determined to be inside a follicle. The processing circuitry 36 grows the seeds into candidate follicle regions. The region identifying circuitry 38 processes the candidate follicle regions to obtain target regions which may be identified as follicles. The region identifying circuitry 38 measures and counts the follicles.

In some embodiments, follicles are automatically measured and counted for many stored medical image data sets, for example in medical image data sets relating to different patients, or to different scans of the same patient. In some embodiments, no input from a user is required in order to measure and count the follicles. It may therefore become practical to measure and count the follicles in a large number of stored data sets.

Although methods are described above with reference to particular apparatuses 20 and 60, any suitable apparatus may be used. The method of any embodiment may be performed using any suitable apparatus or combination of apparatuses. For example, the method of FIG. 4 may be performed using a separate scanner and image processing apparatus. Features of any embodiment may be combined with features of any other embodiment.

The embodiments above are described with reference to the segmentation of follicles. However, in other embodiments, target regions corresponding to any appropriate anatomical structures may be segmented, for example target regions corresponding to cysts or other air or water pockets in other tissue, heart chambers, certain types of tumors or growths, or any other self-contained structures displaying a different overall brightness from the surrounding tissues. In some embodiments, target regions may correspond to hyperechoic tumors, for example liver, spleen, renal and other abdominal metastases. Target regions may be measured and counted. The measurement of target regions may comprise, for example, measuring a diameter, volume or position of a target region.

Although the embodiments above are described with reference to ultrasound, in other embodiments a different modality may be used, for example MR, CT, cone-beam CT, X-ray, PET or SPECT.

Certain embodiments provide a medical imaging method able to detect and measure ovarian follicles comprising pre-processing an image to identify an area of interest and optimize the appearance of the image, growing candidate follicles, and post-processing the result. The pre-processing may comprise any combination of median filtering and anisotropic filtering. Growing candidate follicles may comprise determining statistical distributions for two (inside/outside follicle) or more classes. Growing candidate follicles may comprise determining points inside follicles based on distributions. Growing candidate follicles may comprise using a level set algorithm to grow individual follicles from identified points. Post-processing may comprise any combination of morphological operations to separate wrongly fused follicles or filtering.

Whilst particular circuitries have been described herein, in alternative embodiments functionality of one or more of these circuitries can be provided by a single processing resource or other component, or functionality provided by a single circuitry can be provided by two or more processing resources or other components in combination.

Reference to circuitry encompasses multiple components providing the functionality of that circuitry, whether or not such components are remote from one another, and reference to multiple circuitries encompasses a single component providing the functionality of those circuitries.

Whilst certain embodiments have been described, these embodiments have been presented by way of example only, and are not intended to limit the scope of the invention. Indeed the novel methods and systems described herein may be embodied in a variety of other forms; furthermore, various omissions, substitutions and changes in the form of the methods and systems described herein may be made without departing from the spirit of the invention. The accompanying claims and their equivalents are intended to cover such forms and modifications as would fall within the scope of the invention.

The invention claimed is:

1. A medical imaging data processing apparatus, comprising:
    setting circuitry configured to set a plurality of seeds at different locations in medical image data by distributing the plurality of seeds pseudorandomly or regularly;
    processing circuitry configured to
        estimate, from at least part of the medical image data, a first statistical distribution for pixels or voxels of a target class and at least one further statistical distribution for pixels or voxels of at least one further class;
        select at least one seed from among the plurality of seeds by determining whether each seed belongs to the target class in dependence on the estimated first statistical distribution and the estimated at least one further distribution, and selecting seeds that are determined to belong to the target class, and
        expand the at least one selected seed; and
    region identifying circuitry configured to identify at least one target region based on a result of the expansion, wherein each identified target region comprises tissue belonging to the target class.

2. The apparatus according to claim 1, wherein
    the processing circuitry is further configured to obtain at least one candidate region as a result of the expansion; and
    the region identifying circuitry is further configured to identify the at least one target region based on the at least one candidate region.

3. The apparatus according to claim 1, wherein each identified target region comprises a desired anatomical structure.

4. The apparatus according to claim 1, wherein each obtained candidate region and each identified target region comprises tissue belonging to the target class.

5. The apparatus according to claim 4, wherein each identified target region comprises an ovarian follicle, and the target class comprises follicle tissue.

6. The apparatus according to claim 3, wherein at least one of:
    the region identifying circuitry is further configured to automatically measure each identified target region, thereby to obtain a measurement of the desired anatomical structure;
    the region identifying circuitry is further configured to automatically count each identified target region to count the desired anatomical structure or structures; and
    the region identifying circuitry is further configured to automatically determine a position of each identified target region.

7. The apparatus according to claim 4, wherein expanding the at least one selected seed comprises expanding each selected seed until a boundary between the target class and at least one further class is reached.

8. The apparatus according to claim 4, wherein expanding the at least one selected seed comprises expanding each seed using at least one of a level-set algorithm and a region growing algorithm.

9. The apparatus according to claim 8, wherein the level-set or region growing algorithm is configured to distinguish between the target class and at least one further class based on intensity.

10. The apparatus according to claim 2, wherein at least one of:
   identifying the at least one target region comprises combining two or more adjacent or overlapping candidate regions to form a single candidate region;
   identifying the at least one target region comprises splitting one candidate region into two or more candidate regions; and
   identifying the at least one target region comprises selecting at least one candidate region in dependence on candidate region size and shape.

11. The apparatus according to claim 4, wherein the processing circuitry is further configured to distinguish between the target class and at least one further class.

12. The apparatus according to claim 11, wherein the first statistical distribution and the at least one further statistical distribution each comprise a distribution of at least one of intensity, gradient, shape of the region grown, local gradient, texture appearance indicators, and higher order derivatives.

13. The apparatus according to claim 4, wherein the target class comprises follicle tissue, and wherein the processing circuitry is further configured to distinguish between follicle tissue, tissue between follicles, and tissue outside follicles.

14. The apparatus according to claim 1, further comprising pre-processing circuitry configured to at least one of:
   identify an area of interest in the medical image data; and
   filter at least part of the medical image data using at least one of a noise-reducing filter, an edge-preserving filter, a median filter, and an anisotropic filter.

15. The apparatus according to claim 1, wherein each seed comprises at least one of a point, a pixel, a voxel, a two-dimensional seed region of the area of interest, and a three-dimensional seed region of the area of interest.

16. The apparatus according to claim 1, wherein the medical image data comprises at least one of ultrasound data, CT data, cone-beam CT data, MR data, X-ray data, PET data, and SPECT data.

17. A medical imaging data processing method, comprising:
   setting a plurality of seeds at different locations in medical image data by distributing the plurality of seeds pseudorandomly or regularly;
   estimating, from at least part of the medical image data, a first statistical distribution for pixels or voxels of a target class and at least one further statistical distribution for pixels or voxels of at least one further class;
   selecting at least one seed from among the plurality of seeds by determining whether each seed belongs to the target class in dependence on the estimated first statistical distribution and the estimated at least one further distribution, and selecting seeds that are determined to belong to the target class;
   expanding the at least one selected seed; and
   identifying at least one target region based on the result of the expansion, wherein each identified target region comprises tissue belonging to the target class.

18. A non-transitory computer-readable storage medium storing a computer program comprising computer-readable instructions that are executable to perform a method comprising:
   setting a plurality of seeds at different locations in medical image data by distributing the plurality of seeds pseudorandomly or regularly;
   estimating, from at least part of the medical image data, a first statistical distribution for pixels or voxels of a target class and at least one further statistical distribution for pixels or voxels of at least one further class;
   selecting at least one seed from among the plurality of seeds by determining whether each seed belongs to the target class in dependence on the estimated first statistical distribution and the estimated at least one further distribution, and selecting seeds that are determined to belong to the target class;
   expanding the at least one selected seed; and
   identifying at least one target region based on a result of the expansion, wherein each identified target region comprises tissue belonging to the target class.

19. A medical imaging data processing apparatus, comprising:
   setting circuitry configured to set at least one seed in medical image data by distributing the at least one seed pseudorandomly or regularly;
   processing circuitry configured to
      estimate, from at least part of the medical image data, a first statistical distribution for pixels or voxels of a target class and at least one further statistical distribution for pixels or voxels of at least one further class, the target class being follicles;
      select a seed from among the at least one seed by determining whether each seed belongs to the target class in dependence on the estimated first statistical distribution and the estimated at least one further distribution, and selecting a seed that is determined to belong to the target class, and
      vary an extent of the selected seed to obtain a candidate follicle region; and
   region identifying circuitry configured to process the candidate follicle region to identify at least one follicle.

20. The apparatus according to claim 19, wherein the setting of the at least one seed in the medical image data is in dependence on user input.

21. The apparatus according to claim 19, wherein the region identifying circuitry is further configured to automatically measure each follicle.

22. The apparatus according to claim 19, wherein the region identifying circuitry is further configured to automatically count each follicle.

* * * * *